US008664389B2

(12) United States Patent
Jyothi Prasad et al.

(10) Patent No.: US 8,664,389 B2
(45) Date of Patent: Mar. 4, 2014

(54) PROCESS FOR THE PREPARATION OF LAPATINIB AND IT'S PHARMACEUTICALLY ACCEPTABLE SALTS

(75) Inventors: Ramanadham Jyothi Prasad, Andhra Pradesh (IN); Bhujanga Rao Adibhatla Kali Satya, Andhra Pradesh (IN); Nannapaneni Venkaiah Chowdary, Andhra Pradesh (IN)

(73) Assignee: Natco Pharma Limited, Andhra Pradesh (IN)

( * ) Notice: Subject to any disclaimer, the term of this patent is extended or adjusted under 35 U.S.C. 154(b) by 234 days.

(21) Appl. No.: 13/127,042

(22) PCT Filed: Aug. 12, 2009

(86) PCT No.: PCT/IN2009/000449
§ 371 (c)(1),
(2), (4) Date: Jul. 11, 2011

(87) PCT Pub. No.: WO2010/061400
PCT Pub. Date: Jun. 3, 2010

(65) Prior Publication Data
US 2011/0263852 A1 Oct. 27, 2011

(30) Foreign Application Priority Data
Nov. 3, 2008 (IN) ............................. 2672/CHE/2008

(51) Int. Cl.
*C07C 257/12* (2006.01)
*C07C 251/00* (2006.01)
*C07D 239/94* (2006.01)
*C07D 405/04* (2006.01)
*C07D 407/10* (2006.01)

(52) U.S. Cl.
USPC .......................................... 544/293; 564/245

(58) Field of Classification Search
None
See application file for complete search history.

(56) References Cited

U.S. PATENT DOCUMENTS

| 6,727,256 B1 | 4/2004 | Carter et al. |
| 7,157,466 B2 | 1/2007 | McClure et al. |

FOREIGN PATENT DOCUMENTS

| WO | WO 99/35146 A1 | 7/1999 |
| WO | WO 02/02552 A1 | 1/2002 |
| WO | WO 2005/023783 A1 | 3/2005 |

OTHER PUBLICATIONS

Xia et al., "Anti-tumor activity of GW572016: a dual tyrosine kinase inhibitor blocks EGF activation of EGFR/erbB2 and downstream Erk1/2 and AKT pathways," *Oncogene*, 21:6255-6263 (2002).
Xia et al., "Combining lapatinib (GW572016), a small molecule inhibitor of ErbB1 and ErbB2 tyrosine kinases, with therapeutic anti-ErbB2 antibodies enhances apoptosis of ErbB2-overexpressing breast cancer cells," *Oncogene*, 24:6213-6221 (2005).
Spector, et al., "Study of the Biologic Effects of Lapatinib, a Reversible Inhibitor of ErbB1 and ErbB2 Tyrosine Kinases, on Tumor Growth and Survival Pathways in Patients With Advanced Malignancies," *Journal of Clinical Oncology*, Apr. 2005, vol. 23, No. 11, pp. 2502-2512.
Burris, et al., "Phase I Safety, Pharmacokinetics, and Clinical Activity Study of Lapatinib (GW572016), a Reversible Dual Inhibitor of Epidermal Growth Factor Receptor Tyrosine Kinases, in Heavily Pretreated Patients With Metastatic Carcinomas," *Journal of Clinical Oncology*, Aug. 2005, vol. 23, No. 23, pp. 5305-5313.
Harris, et al., "Antifolate and antibacterial activities of 6-substituted 2,4-diaminoquinazolines," *Eur J Med Chem* (1992) 27, 7-18.

*Primary Examiner* — Sun Jae Loewe
(74) *Attorney, Agent, or Firm* — Kilpatrick Townsend & Stockton LLP (57) ABSTRACT

The present invention relates to an improved and novel process for the preparation of high purity crystalline base of Lapatinib of formula-(1) having chemical name N-{3-chloro-4-[(3-fluorobenzyloxy]phenyl}-6-[5-({[2-(methanesulfonyl)ethyl]amino}methyl]-2-furyl]-4-quin-azolinamine and its pharmaceutically acceptable salts. The present invention further relates to intermediates according to formula (8) and formula (9) used in this process.

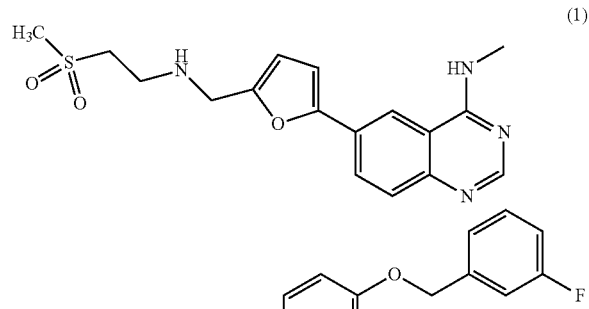

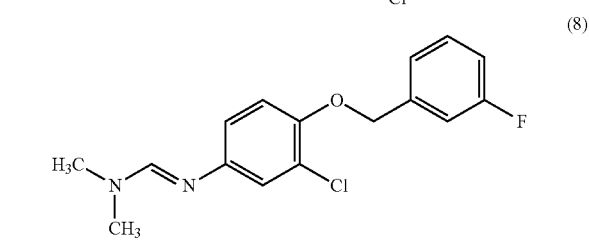

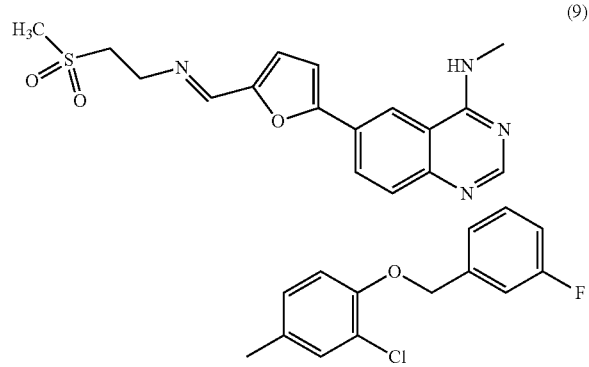

16 Claims, 3 Drawing Sheets

FIGURE-(2)

PROCESS FOR THE PREPARATION OF LAPATINIB AND IT'S PHARMACEUTICALLY ACCEPTABLE SALTS

FIELD OF INVENTION

The present invention relates to an improved and novel process for the preparation of high purity crystalline base of Lapatinib of formula-(1) having chemical name N-{3-Chloro-4-[(3-fluorobenzyloxy]phenyl}-6-[5-({[2-(methanesulfonyl)ethyl]amino}methyl]-2-furyl]-4-quin-azolinamine and its pharmaceutically acceptable salts.

Lapatinib is a molecule that inhibits the activity of both Erb $B_1$ and Erb $B_2$ and has shown clinical activity in breast cancer. As a reversible and dual-acting inhibitor the drug will be able to overcome problems of resistance encountered with single inhibitors.

BACKGROUND OF INVENTION

Lapatinib of formula-(1), is reported for the first time by M. C. Carter et.al in PCT International Publication No.: WO 99/35146 (1999 to Glaxo). Its equivalent US patent is U.S. Pat. No. 6,727,256 (2004 to SmithKline Beecham). Study on mechanism of action of Lapatinib is described in Oncogene, 21, 6255 (2002). In vitro anti-tumor activity in combination with anti-$ErbB_2$ antibodies is described in Oncogene, 24, 6213 (2005), biological effects on tumor growth is described in J. Clin. Oncol, 23, 2502 (2005) and pharmacokinetics and clinical activity in metastatic carcinomas is described in J. clin. oncol, 23, 5305 (2005).

The process for the preparation of Lapatinib of formula-(1), disclosed in WO99/35146, is given in the Scheme-A.

Accordingly, 4-chloro-6-iodo-quinazoline of formula-(2), is reacted with 3-chloro-4-($3^1$-fluoro-benzyloxy)-aniline yielding N-[3-chloro-4-{($3^1$-fluoro-benzyloxy)phenyl}]-6-iodo-quinazoline of formula-(3). The compound of the formula-(3) reacts with (1,3-dioxolan-2-yl)-2-(tributylstannyl)furan to get the compound of formula-(4a) which on reaction with HCl, removes the protecting group and liberates 5-(4-{3-chloro-4-(3-fluoro-benzyloxy)anilino}-6-quinazolinyl)-furan-2-carbaldehyde of formula-(4). The compound of the formula-(4) on reaction with 2-methanesulfonylethylamine, followed by reduction using sodium (triacetoxy)borohydride as the reducing agent gives the required compound Lapatinib of formula-(1) as an organic residue, which is purified by column chromatography. If desired the isolated material is then converted into the hydrochloride salt. 1(a)

SCHEME-A: (WO 99/35146, US 6727256)

In the subsequent PCT-international publication No. WO 02/02552 (glaxo) and its equivalent U.S. Pat. No. 7,157,466; the preparation of ditosylate salts of Lapatinib of formula-1 (b) is disclosed as shown in Scheme-B.

SCHEME-B: (WO 02/02552, US 7157466)

In both of these patents, the process involves multiple steps to get the required product. The process is lengthy and cumbersome and also involves usage of corrosive chemicals like $POCl_3/SOCl_2$ etc.

SUMMARY OF INVENTION

Keeping in view of the difficulties in the above mentioned prior art processes for the preparation of Lapatinib on a commercial scale, we aimed to develop a simple and economically viable and commercially applicable process for the preparation of Lapatinib, of formula-(1).

Accordingly, the main objective of the present invention is to provide an improved process for the preparation of Lapatinib of formula-(1), which is simple, economical and commercially applicable.

According to another objective of the present invention is to provide an improved process for the preparation of Lapatinib of formula-(1), which involves readily and cheaply available raw materials.

According to another objective of the present invention, there is provided a novel compound of the formula-(8) which is an intermediate for the preparation of Lapatinib of the formula-(1) and a process for its preparation.

(8)

According to another objective of the present invention, there is provided a novel compound of the formula-(9) which is an intermediate for the preparation of Lapatinib of the formula-(1) and a process for its preparation.

(9)

During our elaborate research in developing a process for the preparation of Lapatinib of formula-(1) on a commercially viable scale, we observed that commercially and readily available 2-aminobenzonitrile of formula-(6) could be a suitable starting material, when compared to 4-chloro-6-iodo-quinazoline of formula-(2) used in the prior art.

The preparation of key intermediate 2-amino-5-iodobenzonitrile starting from 2-amino benzonitrile is reported by Harris, N. V; Smith, C; et al in Eur. J. Med. Chem. 1992, 27, 7-18. We adopted the same procedure with modifications at recrystallization step for the preparation of 2-amino-5-iodobenzonitrile of formula-(7).

Accordingly, the present invention provides an improved process for the preparation of Lapatinib of formula-(1).

(1)

and its pharmaceutically acceptable salts, which comprises,

(i) Reacting 2-aminobenzonitrile of formula-(6)

(6)

with iodinemonochloride or iodine crystals in acetic acid medium at elevated temperature to get 2-amino-5-iodobenzonitrile of the formula-(7), which is purified by recrystallization from an organic solvent or a mixture of solvents.

(7)

(ii) Reacting 3-chloro-4-(3-fluorobenzyloxy)-aniline of formula-(7a)

(7a)

with N,N-dimethylformamide dimethyl acetal in an organic solvent and at an elevated temperature yielding the novel compound of the formula-(8)

(8)

(iii) Coupling the compound of the formula-(7) with the novel compound of the formula-(8) in presence of an acid catalyst and at an elevated temperature to get a compound of the formula-(3).

(3)

(iv) Reacting the compound of the formula-(3) with 5-formyl-2-furyl boronic acid by palladium (O) mediated biaryl coupling (Suzuki cross coupling) in an ethereal solvent at an elevated temperature to get the desired compound of formula-(4).

(4)

(v) Reacting the compound of the formula-(4), with 2-methanesulfonylethylamine or its salt in a suitable solvent, at an elevated temperature gives the novel imine compound of the formula-(9).

(9)

(vi) Reacting the compound of the formula-(9) with a suitable reducing agent in a suitable solvent and the resultant amine formed is extracted with a suitable solvent and subsequent evaporation of the solvent gives Lapatinib base of the formula-(1)

(vii) Crystallizing the crude Lapatinib base of formula-(1) from a suitable solvent to get pure Lapatinib base.

(viii) Reacting pure Lapatinib base of formula-(1) by dissolving or suspending in an organic solvent with p-toluenesulfonicacid monohydrate to get Lapatinib ditosylate (anhydrous) of formula-1(b)

(ix) Recrystallization of Lapatinib ditosylate (anhydrous) in aqueous alcohol affords pharmaceutically acceptable grade Lapatinib ditosylate monohydrate of formula-1(c).

Accordingly, the basic raw material selected for the synthesis of Lapatinib of formula-(1) is commercially available 2-amino benzonitrile of formula-(6), which reacts with iodine or iodinemonochloride to get 2-amino-5-iodobenzonitrile of the formula-(7). The compound of the formula-(7) on reaction with a novel compound $N^1$-(3-chloro-4-(3-fluorobenzyloxy)phenyl)-N,N-dimethylformamidine (8) at elevated temperature gives the compound N-[3-chloro-4-[(3-fluorobenzyloxy)phenyl]-6-iodo-quinazolinamine of formula-(3), The compound of the formula-(3) on reaction with 5-formyl-2-furyl boronic acid, in presence of triethylamine and Pd/C gives the compound 5-[4-[3-chloro-4-(3-fluorobenzyloxy)anilino]-6-quinazolinyl)-furan-2-carbaldehyde of the formula-(4). The compound of the formula-(4), on reaction with 2-methanesulfonylethylamine hydrochloride gives the novel compound N[3-chloro-4[(3-fluorobenzyloxy]phenyl[-6-[5-({[2-methanesulphonyl)-ethyl]imino}-2-furyl]-4-quinazolinamine of the formula-(9). The novel imine compound of formula-(9) on reduction, using sodium borohydride gives the compound of the formula-(1), which is Lapatinib base. The reaction scheme of the present invention is as given the following Scheme-(C).

DETAILED DESCRIPTION OF INVENTION

In a preferred embodiment of the present invention (SCHEME-C),

In the step (i), 2-aminobenzonitrile of the formula-(6) is reacted with iodinemonochloride in acetic acid medium to get the compound of the formula-(7). During the reaction, the reaction temperature is maintained at 0 to 100° C., preferably between 10 to 50° C., most preferably between 25 to 35° C. The organic solvent used for purification by recrystallization, is a mixture of toluene and hexane.

In the step (ii), the reaction of 3-chloro-4-(3-fluorobenzyloxy)-aniline of formula-(7a), with N,N-dimethylformamide dimethylacetal may be carried out in presence of a suitable solvent or diluent, for example in an aromatic solvent such as toluene, xylene, cumene or chlorobenzene, or in a polar aprotic solvent such as acetonitrile, propionitrile, butyronitrile, ethylacetate, tetrahydrofuran, 2-methyl tetrahydrofuran, 1,4-dioxan or a dipolar aprotic solvent such as N,N-dimethylformamide, N,N-dimethyacetamide, N-methylpyrrolidin-2-one or dimethylsulfoxide. A further suitable solvent or diluent is water or a polar protic solvent such as as a primary secondary or tertiary alkyl alcohol, for example, methanol, ethanol, 2-propanol, a butanol or pentanol. Mixtures of such suitable solvents or diluents may be used.

Conveniently, the reaction is carried out in an organic solvent, for example toluene or xylene preferably toluene and at a temperature in between 30 to 150° C., preferably between 80 to 110° C.

The product is obtained by evaporation of the solvent followed by adding a solvent like hexane, heptane or a mixture thereof preferably hexane. The product isolation temperature is in between 0 to 40° C., preferably 0 to 5° C.

In the step (iii), the compound of formula-(7) is coupled with novel compound of formula-(8) in the presence of acid catalyst which is selected from trifluoro acetic acid, formic acid or acetic acid, preferably acetic acid, in polar aprotic or dipolar aprotic or aromatic solvents like toluene, xylene, cumene etc. preferably xylene at a temperature range between 30-140° C., preferably 130-135° C.

In the step (iv), in Suzuki coupling reaction, the ethereal solvent used is selected from diethyl ether, tetrahydrofuran, 1,4-dioxane, 1,2-diethoxyethane and 1,2-dimethoxy ethane, preferably 1,2-dimethoxy ethane (DME).

The catalyst used is selected from a list that includes palladium (II) acetate, palladium (II) chloride, palladium on carbon, preferably palladium on carbon.

The reaction temperature is in between 25 to 120° C. preferably between 25 to 75° C. and most preferably between 45-50° C.

In the step-(v), the aldehyde compound of formula-(4) is reacted with 2-methanesulphonyl ethylamine or its salts with acids like HCl, HBr or $H_2SO_4$, preferably HCl salt. The solvent used for the reaction includes dichloroethane, dichloromethane, tetrahydrofuran, 2-methyl tetrahydrofuran, N,N-dimethyl Formamide, 1,2-dimethoxyethane and alcohols like ethanol, methanol, 2-propanol or a mixture thereof. The preferred solvents are tetrahydrofuran and methanol, most preferably methanol.

The reaction temperature is in between 0 to 125° C. preferably between 25 to 100° C. and most preferably the reflux temperature of methanol.

In the step-(vi), for the reduction of imine of formula-(9) to amine, the reducing agent used is selected from sodiumtriacetoxyborohydride, sodium borohydride etc, preferably sodium borohydride.

Solvent used in the reaction can be selected from tetrahydrofuran, acetonitrile, acetone, dimethylformamide, dimethylacetamide, 1,2-diethoxyethane, 1,2-dimethoxyethane or a mixture thereof, preferably a mixture of tetrahydrofuran and methanol. The reaction temperature is in between 0 to 100° C. preferably 0 to 40° C. most preferably 0 to 15° C.

The reaction mass is decomposed with water and extracted with solvents like ethylacetate, methylacetate, isopropylacetate, dichloroethane, dichloromethane, chloroform, tertiary butyl methyl ether etc. preferably ethylacetate. The crude product is obtained by solvent evaporation.

In the step-(vii), the obtained crude Lapatinib base is purified by crystallization from different solvents like ethylacetate, methylacetate, isopropyl acetate, acetonitrile, methanol, ethanol, isopropanol, acetone, methylethylketone, methylenechloride, toluene, chloroform, 1,4-dioxane, dimethylfromamide, tetrahydrofuran, 2-methyltetrahydrofuran, dimethylacetamide, 1,2-dimethoxyethane, tertiarybutylmethyl ether, water or a mixture thereof, preferably ethylacetate, isopropanol and methanol.

The isolation temperature of recrystallized Lapatinib base is 0 to 35° C. preferably 25-35° C.

The purity of Lapatinib base obtained according to process of the present invention is more than 99.5% by HPLC.

Figure 2:
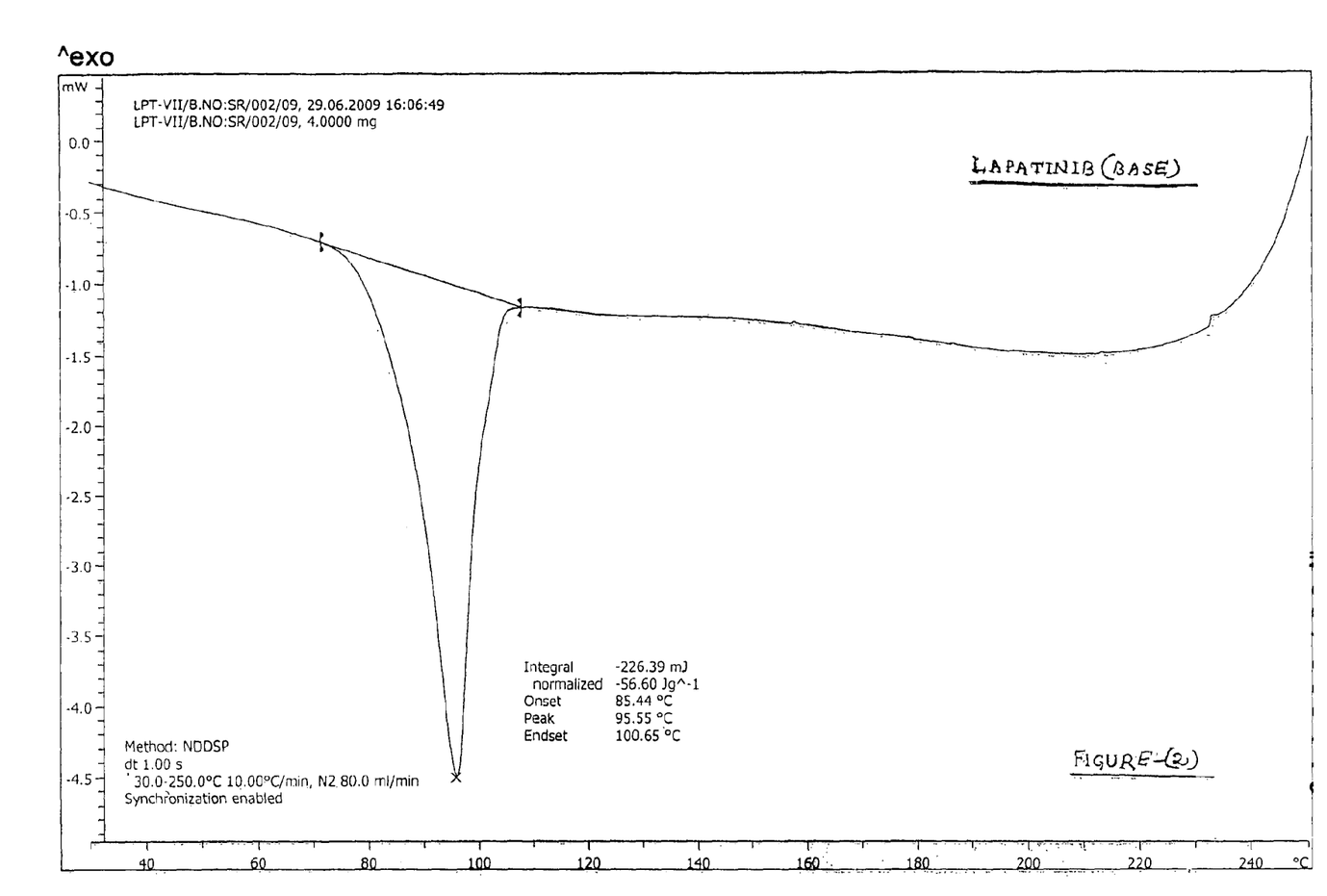
FIG. 2: Illustrates DSC thermogram of Lapatinib base

The melting point range of the pure Lapatinib base obtained is 95-98° C. (peak max. by DSC)

Figure 3:
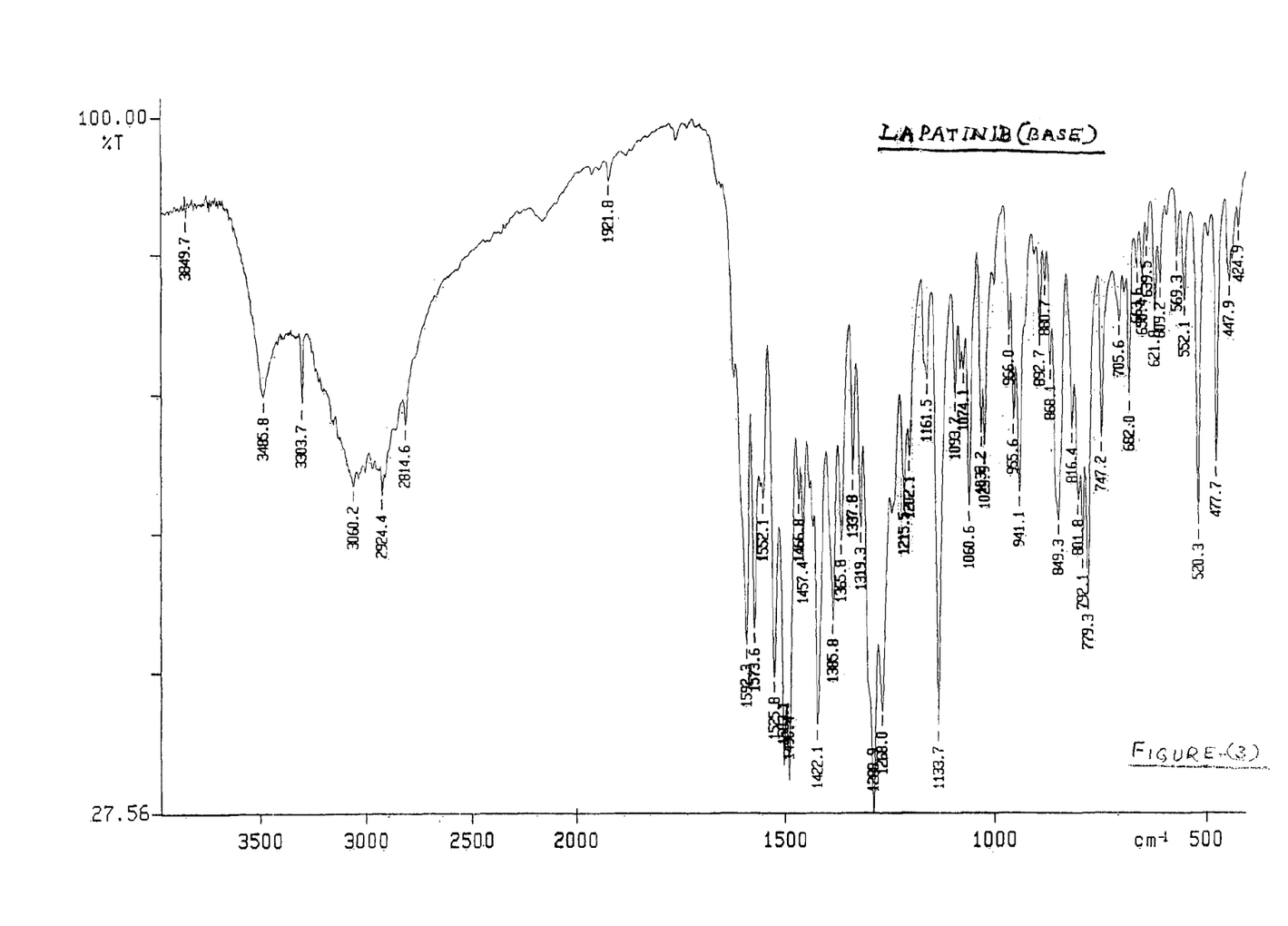
FIG. 3: Illustrates IR pattern of Lapatinib base

The IR spectral values of pure Lapatinib base obtained are 3485.8, 3303.7, 3060.2, 2924.4, 2814.6, 1921.8, 1592.3, 1573.6, 1525.8, 1490.4, 1457.4, 1422.1, 1385.8, 1365.8, 1337.8, 1319.3, 1288.9, 1268.0, 1215.5, 1133.7, 1060.6, 1029.9, 941.1, 849.3, 779.3, 747.2, 682.0, 552.1, 520.3, 477.7 $cm^{-1}$.

Figure 1:
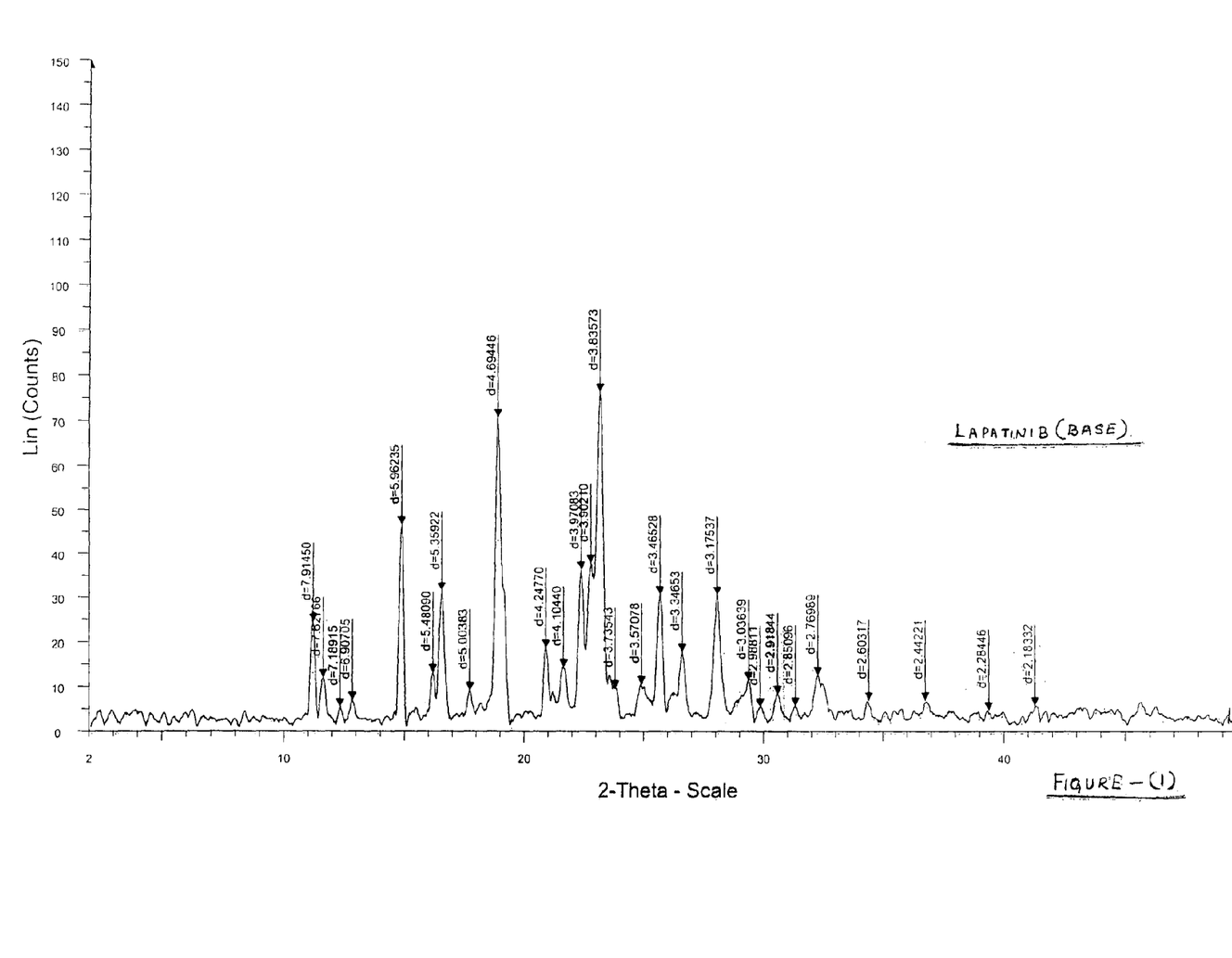
FIG. 1: Illustrates the powder X-ray diffraction pattern of Lapatinib base

The 2θ values of powder XRD of pure Lapatinib base obtained are 11.17, 11.59, 12.30, 12.80, 14.84, 16.15, 16.52, 17.71, 18.88, 20.89, 21.63, 22.37, 22.77, 23.17, 23.80, 24.91, 25.68, 26.61, 28.07, 29.39, 29.87, 30.60, 31.35, 32.29, 34.42, 36.77, 39.41, and 41.31.

In the step-(viii), the purified Lapatinib base so obtained can be converted into ditosylate salt (anhydrous) by suspending or dissolving the Lapatinib base in an organic solvent or a mixture of organic solvents and then treating with p-toluenesulfonicacid monohydrate.

The organic solvent used for dissolving or suspending the Lapatinib base is selected from toluene, chloroform, isopropanol, ethanol, methanol, acetone, methyethylketone, acetonitrile methylacetate, ethylacetate, isopropylacetate, dimethylformamide, dimethylether, diethylether, tertiarybutylmethylether, tetrahydrofuran, 2-methyltetrahydrofuran, dimethylacetamide, 1,2-diethoxyethane, 1,2-dimethoxyethane or a mixture thereof, preferably tetrahydrofuran, methanol or most preferably methanol.

The reaction temperature during ditosylate salt formation is in between 0 to 80° C., preferably the refluxing temperature of the solvent used. The isolation temperature is in between 0 to 35° C. preferably 25-35° C.

In step-(ix), Lapatinib ditosylate monohydrate is obtained by suspending or dissolving Lapatinib ditosylate (anhydrous) in a mixture of water and organic solvents like ethanol, methanol, isopropanol, N,N,dimethylformide, tetrahydrofuran, 2-methyltetrahydrofuran, acetonitrile, acetone, methylethylketone, methylenechloride, preferably tetrahydrofuran and water mixture or isopropylalcohol and water mixture, most preferably isopropylalcohol and water mixture.

The content of water in aqueous isopropylalcohol is in between 5 to 50% preferably 30% v/v.

Lapatinib ditosylate monohydrate so obtained is more than 99.9% pure by HPLC.

The crystalline Lapatinib ditosylate monohydrate so obtained has a mean particle size ($D_{50}$) ranging from about 5 µm to 15 µm and 90 volume % of the particles ($D_{90}$) ranging from 30 µm to 60 µm.

Advantages:
1) Lapatinib and its Pharmaceutically acceptable ditosylate salt obtained by this process is of high purity (99.9%).
2) The present process does not require any chromatographic purification.
3) The present process involves novel compounds of the formula-(8) and formula-(9) contributing to elegance of the overall synthetic scheme.
4) In the present process the number of discrete synthetic steps is reduced.

The details of the invention are given in the examples below which are provided to illustrate the invention only and therefore should not be construed to limit the scope of the present invention.

Example-1

Preparation of $N^1$-(3-chloro-4-(3-fluorobenzyloxy) phenyl)-N,N-dimethyl formamidine (8)

Into a one liter four necked round bottomed flask, 500 mL of toluene, 50.0 g of 3-chloro-4-(3-fluoro-benzyloxy)-aniline, 50.0 g of dimethylformamide dimethyl acetal and 3.0 mL of acetic acid were charged under stirring. The reaction mixture was maintained at reflux temperature for about 2 hrs and the completion of the reaction was monitored by TLC. The solvent was completely distilled off under vacuum, the resulting syrupy liquid was cooled to room temperature. To this 200 mL of water was added and adjusted to basic pH by adding dilute sodium hydroxide solution. The product was extracted into ethylacetate and separated the organic layer. The organic layer was clarified by carbon treatment and filtered. The filtrate was completely distilled off under vacuum. The mass was cooled to room temperature and added 250 mL of hexane and stirred at 0 to 5° C. for about two hours to crystallize the product. The product was filtered and dried under vacuum at 30-35° C. to get 58.0 gram (95% by theory) of $N^1$-(3-chloro-4-(3-fluorobenzyloxy)phenyl)-N,N-dimethylformamidine as a white crystalline powder.

Purity: 99.66% by HPLC
Melting-range: 45-47° C.
Mass: 307.5 [M+1]
IR (KBr, cm$^{-1}$): 2917, 2798, 2364, 1637, 1591, 1557, 1500, 1453, 1410, 1373, 1269, 1250, 1205, 1137, 1103, 1059, 1016, 926, 877, 859, 809, 772, 749, 704, 680, 637, 606, 519.
$^1$H-NMR (400 MHz; DMSO-D$_6$): δ 2.87 (s, 3H); δ 2.98 (s, 3H); δ 5.15 (s, 2H); δ 6.80-6.83 (dd, 1H); δ 6.99-7.00 (d, 1H); δ 7.04-7.06 (d, 1H); 7.14-7.18 (m, 1H); δ 7.26-7.30 (m, 2H); δ 7.42-7.47 (m, 1H); δ 7.72 (s, 1H)
$^{13}$C-NMR (400 MHz; DMSO-D$_6$): δ 33.90 (2C), 69.56, 114.0, 115.19, 120.21, 121.51, 121.90, 123.20, 130.45, 140.02, 146.71, 148.41, 153.76, 160.97, and 163.39.

Hydrochloride Salt:
A 5.0 g sample was taken in a three necked round bottomed flask and dissolved in 50 mL of ethylacetate and added 1.1 equivalents of HCl as isopropyl alcohol HCl and refluxed for one hour. The mixture was cooled to room temperature, filtered and dried.

Melting-range: 228-229° C.
Purity: 99.8% by HPLC

Example-2

Preparation of N{3-chloro-4-[(3-fluorobenzyloxy] phenyl}-6-[5-({[2-methanesulphonyl)ethyl] amino}methyl)-2-furyl]-4-quinazolinamine. (or) Lapatinib base (1)

(i) Preparation of 2-amino-5-iodobenzonitrile (7)

Into a one liter four necked round bottomed flask, acetic acid (200 mL), 2-aminobenzonitrile (30.0 g) were charged. To this reaction mass, iodinemonochloride (44 g) in acetic acid (200 mL) solution was added drop-wise at 25-35° C. The reaction mass was maintained at 25-35° C. for about 3 hrs. The completion of the reaction was monitored by TLC. The reaction mass was poured into ice cold water, stirred for 1 hour and filtered and dried under vacuum to get 55.0 g of brick-red coloured powder.

Purity: 97.1% by HPLC
To enhance the purity of the product the following recrystallization process was adopted.

Purification:
Into a two liter four necked round bottomed flask, 275 mL of toluene and 55 g of crude 2-aminobenzonitrile as obtained above were charged. The mass was stirred for 30 min and clarified with activated carbon (5 g) and filtered. To the filtrate 825 mL of hexane was added and stirred for 1 hr. at 25-30° C. to crystallize out the product. The product was filtered and dried under vacuum at 30-40° C. to get 46.5 g of 2-amino-5-iodobenzonitrile as a pinkish coloured crystalline powder.

Melting-range: 85 to 87° C.
Purity: 99.89% by HPLC (ii) Preparation of N-[3-chloro-4-[(3-fluorobenzyloxy)phenyl]-6-iodo-quinazolin amine (3)

Into a one liter four-necked round bottomed flask, 500 mL of xylene, 50.0 g of $N^1$-(3-chloro-4-(3-fluorobenzyloxy)phenyl)-N,N-dimethylformamidine obtained by the process given in example-(1), 40 g of 2-amino-5-iodobenzonitrile obtained by the process given in above step (i) and 25 mL of acetic acid were charged under stirring. The reaction was maintained at reflux condition for 10 hours and the completion of the reaction was monitored by TLC. The solvent was distilled off completely under vacuum and cooled to room temperature. 100 mL of isopropylalcohol was added and adjusted the pH to basic (about 10) with aqueous ammonia solution. The mass was maintained at that temperature for about 1 hr. The mass was cooled to room temperature and filtered and dried to get 70.0 g of N-[3-chloro-4-[(3-fluorobenzyloxy)phenyl]-6-iodo-quinazolinamine as a pale yellow coloured crystalline powder.

Purity: 99.43% by HPLC
Melting point range: 222-225° C.

(iii) Preparation of 514-[3-chloro-4-(3-fluorobenzyloxy)-anilino]-6-quinazolinyl)-furan-2-carbaldehyde (4)

Into a two liter four-necked round bottomed flask, 1000 mL of 1,2-dimethoxyethane, 50.0 g of N-(3-chloro-4-(3-fluorobenzyloxy)phenyl)-6-iodo-quinazolinamine obtained from the previous step (ii), 5-formyl-2-furyl boronicacid (21.5 g), triethylamine (30.5 g), 10% Pd on carbon (wet) (2.5 g) suspended in 500 mL of methanol were charged under stirring. The mass was maintained at 45-50° C. for about 15 hours under nitrogen atmosphere and the completion of the reaction was monitored by TLC. The catalyst was filtered and the filtrate was quenched into two liters of water and stirred well. The product was filtered and dried to get 45.0 g (96% of theory) of 5-[4-3-chloro-4-(3-fluorobenzyloxy)-anilino]-6-quinazolinyl)-furan.-2-carbaldehyde as a greenish yellow amorphous powder.

Purity: 99.6% by HPLC
Melting range: 224-228° C.

(iv) Preparation of N-{3-chloro-4-[(fluorobenzyloxy]phenyl}-6-[5-({[2-methane-sulphonyl)ethyl]imino}methyl)-2-furyl]-4-quinazolinamine (9)

Into a two liter four-necked round bottomed flask, 1000 mL of methanol, 40.0 g of N-(3-chloro-4-(3-fluorobenzyloxy)anilino)-6-quinazolinyl)-furan-2-carbadehyde, obtained from the previous step (iii), 20.6 g of 2-methanesulfonylethylamine HCl and 13.4 g of triethylamine were charged under stirring. The mass was maintained at reflux temperature for about 12 hours and the reaction was monitored by HPLC. The reaction mass was cooled to room temperature and filtered. The product was dried under vacuum at room temperature to get 47.0 g (96% of theory) of imine as yellow coloured crystalline solid. The product was stored under nitrogen atmosphere.

Melting point range: 74 to 76° C.
Purity: 99.0% by HPLC
Mass: 580.1 (M+1)
IR (KBr, cm$^{-1}$): 3339.7, 2928.0, 2362.4, 1637.3, 1608.6, 1593.4, 1572.1, 1539.1, 1497.9, 1445.9, 1425.6, 1394.3, 1371.0, 1330.5, 1294.8, 1216.9, 1198.2, 1171.6, 1123.8, 1061.4, 1026.5, 956.6, 927.8, 888.3, 868.1, 839.9, 789.7, 748.5, 679.9, 643.2, 628.7, 544.4, 517.6, 501.5.
$^1$H-NMR (400 MHz, DMSO-D$_6$): δ 3.06 (s, 3H); 3.51-3.53 (t, 2H), 3.96-3.98 (t, 2H); 5.27 (s, 2H); 7.19-7.20 (m, 2H); 7.20-7.33 (m, 4H); 7.47-7.49 (m, 1H), 7.71-7.74 (dd, 1H), 7.83-7.85 (d, 1H); 8.00-8.01 (m, 1H); 8.22-8.24 (dd, 1H); 8.33 (s, 1H); 8.58 (s, 1H); 8.86 (s, 1H) and 10.03 (s, 1H)
$^{13}$C-NMR (400 MHz, DMSO-D$_6$): δ 41.84, 53.92, 54.31, 69.40, 109.25, 113.93, 114.15, 114.32, 114.61, 114.82, 115.35, 117.63, 121.08, 123.33, 124.40, 129.03, 130.62, 132.95, 139.60, 139.68, 149.52, 149.87, 151.17, 151.79, 154.80, 157.73, 161.01, 164.02, 169.05

(v) Preparation of N{3-chloro-4-[(3-fluorobenzyloxy]phenyl}-6-[5-({[2-methanesulphonyl)ethyl]amino}methyl)-2-furyl]-4-quinazolinamine (or) Lapatinib base (1)

Into a two liter four-necked round bottomed flask, 400 mL of tetrahydrofuran, 40 g of imine obtained from the previous step-(iv), 400 ml of methanol were charged under stirring. The reaction mass was cooled to 0 to 5° C. and 7.0 g of sodium borohydride was added in lots and the reaction mass was maintained for about 4 hrs at 10 to 15° C. The completion of the reaction was monitored by HPLC. To this reaction mass 800 ml of water was added and the product was extracted into ethylacetate. The organic layer was separated and the solvent distilled off completely under vacuum. The solvent was distilled off completely under vacuum. The residue was cooled to 25-35° C. and 80 mL of ethylacetate was added, stirred for 2 hrs, filtered and dried under vacuum at 40-45° C. to get 30.5 g (75% on theory) of crude Lapatinib base.

Purity: 90% by HPLC

The purity of the above product was enhanced by adopting the following procedure.

Purification:

Into a two liter four-necked round-bottomed flask; 1200 mL of methanol, 30.0 g of Lapatinib crude base obtained as above were charged under stirring. The mass was maintained at 60-65° C. for 30-45 minutes and filtered the undissolved material. The filtrate was distilled off completely under vacuum. The mass was cooled to 25-35° C. To the residue 60 mL of methanol was added, stirred for 2 hrs, filtered and dried the product under vacuum at 40-45° C. to get 28 g of pure Lapatinib base.

Purity: 99.5% by HPLC
Melting point range: 95-98° C. (Peak maximum by DSC)
IR (KBr, cm$^{-1}$): 3485.8, 3303.7, 3060.2, 2924.4, 2814.6, 1921.8, 1592.3, 1573.6, 1525.8, 1490.4, 1457.4, 1422.1, 1385.8, 1365.8, 1337.8, 1319.3, 1288.9, 1268.0, 1215.5, 1133.7, 1060.6, 1029.9, 941.1, 849.3, 779.3, 747.2, 682.0, 552.1, 520.3, 477.7.
2θ values by XRPD: 11.17, 11.59, 12.30, 12.80, 14.84, 16.15, 16.32, 17.71, 18.88, 20.89, 21.63, 22.37, 22.77, 23.17, 23.80, 24.91, 25.68, 26.61, 28.07, 29.39, 29.87, 30.60, 31.35, 32.29, 34.42, 36.77, 39.41, and 41.31.

(vi) Preparation of N-{3-chloro-4-[(3-fluorobenzyloxy]phenyl}-6-[5-({[2-methane sulphonyl)ethyl]amino}methyl)-2-furyl]-4-quinazolinamine ditosylate salt (or) Lapatinib ditosylate (anhydrous) 1(b)

Into a two liter four-necked round bottomed flask, 1500 mL of methanol, 25 g of Lapatinib base, obtained from the previous step-(v) were charged. The mass temperature was raised to 60-65° C. to dissolve the solid completely, and then cooled to 45-50° C. and 18 g of p-toluenesulphonicacid monohydrate dissolved in 50 mL of methanol was added. The reaction mass was maintained at reflux condition for 3 hrs, cooled to 25-35° C. and filtered. The product was dried under vacuum at 75-80° C. to get 35 g (88% of theory) of Lapatinib ditosylate salt as an yellow crystalline solid.

Melting point range: 237-239° C.
Purity: 99.8% by HPLC

(vii) Preparation of N{3-chloro-4-[(3-fluorobenzyloxy]phenyl}-6-5-({[2-methane sulphonypethyl]amino}methyl)-2-furyl]-4-quinazolinaminediтosylate monohydrate (or) Lapatinib ditosylate monohydrate 1(c)

Into a two liter four-necked round bottomed flask, 1000 mL of 70% isopropylalcohol in water, 25 g of Lapatinib ditosylate salt obtained from previous step-(vi) were charged. The mass temperature was raised to 75 to 80° C. and stirred for 20-30 minutes to dissolve the product completely. Then solution was clarified by carbon treatment and filtered. The filtrate was cooled to 30-35° C. under stirring. The product was filtered and dried at 70-75° C. under vacuum till water content was around 2% w/w to get 23.0 g of yellow coloured Lapatinib ditosylate monohydrate.

Purity: 99.9% by HPLC
Water content: 2.0% w/w (1.91% w/w by theory)
Particle size range: $D_{50}$: 5-15 µm and $D_{90}$: 30-60 µm

We claim:
1. An isolated compound of formula (9):

or a pharmaceutically acceptable salt thereof.

2. A method for the preparation of Lapatinib of formula (I)

or a pharmaceutically acceptable salt thereof which method comprises the hydrogenation of a compound of formula (9) or the derivitization of a compound of formula (8), wherein the compound of formula (9) is obtained by reacting N-(3-chloro-4-(3-fluorobenzyloxy)aniline)-6-quinazolinyl)-furan-2-carbaldehyde with 2-methane sulfonylethylamine HCl and triethylamine in methanol at reflux temperature, cooling the reaction mass to room temperature, filtering, and drying under vacuum at room temperature.

3. A method which comprises:

(i) reacting 2-aminobenzonitrile of formula-(6)

(6)

with iodinemonochloride or iodine crystals in acetic acid medium at elevated temperature to get 2-amino-5-iodo-benzonitrile of the formula-(7), which is purified by recrystallization from an organic solvent or a mixture of solvents; and (7)

(ii) reaction of 3-chloro-4-(3-fluorobenzyloxy)-aniline of formula-(7a)

(7a)

with N,N-dimethylformamide dimethyl acetal in an organic solvent and at an elevated temperature to yield the compound of the formula-(8)

(8)

4. A method which comprises:

(i) reacting a compound of formula-(3) with 5-formyl-2-furyl boronic acid by palladium (0) mediated biaryl coupling in an ethereal solvent at an elevated temperature to get the desired compound of formula-(4); and (3)

(4)

(ii) reacting the compound of the formula-(4), with 2-methane sulfonylethylamine or its salt in a suitable solvent, to give the amine compound of the formula-(9)

(9)

5. A method according to claim 4, which further comprises
(iii) reacting the compound of the formula-(9) with a suitable reducing agent in a suitable reaction solvent and extracting the resultant amine formed with a suitable extraction solvent and subsequently evaporating solvent to give Lapatinib base of the formula-(1);

(1)

(iv) crystallizing the crude Lapatinib base of formula-(1) from a suitable solvent to get pure Lapatinib base;

(v) reacting pure Lapatinib base of formula-(1) by dissolving or suspending in an organic solvent with p-toluenesulfonicacid monohydrate to obtain anhydrous Lapatinib ditosylate of formula-1(b); and (1b)

(vi) recrystallization of anhydrous Lapatinib ditosylate in aqueous alcohol to obtain pharmaceutically acceptable grade Lapatinib ditosylate monohydrate of formula-1(c):

(1c)

6. A method according to claim 3 wherein, in step-(i):
(a) during iodination of 2-aminobenzonitrile, the reaction temperature is maintained at 0 to 100° C.; and/or
(b) during iodination of 2-aminobenzonitrile, the organic solvent used for purification by recrystallization, is a mixture of toluene and hexane.

7. A method according to claim 3 wherein, in step-(ii):
(a) the solvent used for the reaction is selected from toluene, xylene, cumene, chlorobenzene, acetonitrile, propionitrile, butyronitrile, ethylacetate, tetrahydrofuran, 2-methyltetrahydrofuran, 1,4-dioxane, N,N-dimethylformamide, N,N-dimethyacetamide, N-methyl-pyrrolidin-2-one, dimethylsulfoxide, water, methanol, ethanol, 2-propanol, butanol, pentanol or a mixture thereof; and/or
(b) the reaction temperature is between 30 and 150° C.; and/or
(c) the compound of formula 8 is further isolated using a solvent selected from hexane, heptane or a mixture thereof; and/or
(d) the compound of formula 8 is further isolated using an isolation temperature between 0 and 40° C.

8. A method according to claim 4 wherein, prior to step (i):
(a) the compound of formula-(7) is coupled with novel compound of formula-(8) in the presence of an acid catalyst which is selected from trifluoroacetic acid, formic acid or acetic acid, to obtain a compound of formula (3); and wherein
  i. the solvent used for the reaction is selected from toluene, xylene, or cumene; and/or
  ii. the reaction temperature is between 30 and 140° C.

9. A method according to claim 4 wherein, in step-(i):
(a) in palladium (0) mediated biaryl coupling reaction, the ethereal solvent used is selected from diethylether, tetrahydrofuran, 1,4-dioxane, 1,2-diethoxyethane or 1,2-dimethoxyethane; and/or
(b) a palladium catalyst is used and is selected from palladium (II) acetate, palladium (II) chloride, or palladium on carbon; and/or
(c) the reaction temperature is between 25 and 120° C.

10. A method according to claim 4 wherein, in step-(ii):
(a) the compound of the formula-(4) is reacted with 2-methanesulphonyl ethylamine or an HCl, HBr or $H_2SO_4$ salt thereof; and/or
(b) the solvent used for the reaction includes dichloroethane, dichloromethane, tetrahydrofuran, 2-methyl tetrahydrofuran, N,N-dimethylformamide, 1,2-dimethoxyethane, ethanol, methanol, 2-propanol or a mixture thereof; and/or
(c) the reaction temperature is between 0 and 125° C.

11. A method according to claim 5 wherein, in step-(iii):
(a) the reducing agent used is selected from sodiumtriacetoxyborohydride or sodiumborohydride; and/or
(b) the reaction solvent used is selected from tetrahydrofuran, acetonitrile, acetone, dimethylformamide, dimethylacetamide, 1,2-diethoxyethane, 1,2-dimethoxyethane or a mixture thereof; and/or
(c) the reaction temperature is between 0 and 100° C.; and/or
(d) the extraction solvent is selected from ethylacetate, methylacetate, isopropylacetate, tertiarybutylmethylether, dichloroethane, dichloromethane, or chloroform.

12. A method according to claim 5 wherein, in step-(iv):
(a) the solvent used for purification of Lapatinib crude base by crystallization is selected from ethylacetate, methylacetate, isopropylacetate, acetonitrile, methanol, ethanol, isopropanol, acetone, methylethylketone, methylenechloride, toluene, chloroform, 1,4-dioxane, dimethyl formamide, tetrahydrofuran, 2-methyltetrahydrofuran, dimethylacetamide, 1,2-dimethoxyethane, tertiarybutylmethylether, water or a mixture thereof; and/or
(b) an isolation temperature for crystallized Lapatinib base is between 0 and 35°; and/or
(c) the purity of Lapatinib base obtained is more than 99.5% by HPLC; and/or
(d) the melting point range of the pure Lapatinib base obtained is 95-98° C.; and/or
(e) the 2θ values of powder XRD of pure Lapatinib base obtained are 11.17, 11.59, 12.30, 12.80, 14.84, 16.15, 16.52, 17.71, 18.88, 20.89, 21.63, 22.37, 22.77, 23.17, 23.80, 24.91, 25.68, 26.61, 28.07, 29.39, 29.87, 30.60, 31.35, 32.29, 34.42, 36.77, 39.41, and 41.31; and/or
(f) the IR spectral values of pure Lapatinib base obtained are 3485.8, 3303.7, 3060.2, 2924.4, 2814.6, 1921.8, 1592.3, 1573.6, 1525.8, 1490.4, 1457.4, 1422.1, 1385.8, 1365.8, 1337.8, 1319.3, 1288.9, 1268.0, 1215.5, 1133.7, 1060.6, 1029.9, 941.1, 849.3, 779.3, 747.2, 682.0, 552.1, 520.3, 477.7 cm$^{-1}$.

13. A method according to claim 5 wherein, in step-(v):
(a) the organic solvent used for dissolving or suspending pure Lapatinib base is selected from toluene, chloroform, isopropanol, ethanol, methanol, acetone, methyethylketone, acetonitrile, methylacetate, ethylacetate, isopropylacetate, dimethylformamide, dimethylether, diethylether, tertiarybutylmethylether, tetrahydrofuran, 2-methyltetrahydrofuran, dimethylacetamide, 1,2-diethoxyethane, 1,2-dimethoxyethane or a mixture thereof; and/or
(b) a reaction temperature during ditosylate salt formation is between 0 and 80° C.; and/or
(c) an isolation temperature for ditosylate salt formed is between 0 and 35° C.

14. A method according to claim 5 wherein, in step-(vi):
(a) Lapatinib ditosylate monohydrate is obtained by suspending or dissolving anhydrous Lapatinib ditosylate in a mixture of water and an organic solvents selected from ethanol, methanol, isopropanol, N,N,dimethylformide, tetrahydrofuran, 2-methyltetrahydrofuran, acetonitrile, acetone, methylethylketone, or methylenechloride; and/or
(b) the Lapatinib ditosylate monohydrate obtained is of purity more than 99.9% by HPLC; and/or
(c) the crystalline Lapatinib ditosylate monohydrate so obtained has a particle size ranging from about 5 μm to 15 μm and 90 volume % of the particles ranging from 30 μm to 60 μm.

15. A compound of formula (8)

(8)

16. A method according to claim 4, wherein the compound of formula (9) is obtained by reacting N-(3-chloro-4-(3-fluorobenzyloxy)aniline)-6-quinazolinyl)-furan-2-carbaldehyde (4) with 2-methane sulfonylethylamine HCl and triethylamine in methanol at reflux temperature, cooling the reaction mass to room temperature, filtering, and drying under vacuum at room temperature.

* * * * *

UNITED STATES PATENT AND TRADEMARK OFFICE
CERTIFICATE OF CORRECTION

PATENT NO. : 8,664,389 B2  
APPLICATION NO. : 13/127042  
DATED : March 4, 2014  
INVENTOR(S) : Prasad et al.

It is certified that error appears in the above-identified patent and that said Letters Patent is hereby corrected as shown below:

On the Title Page, item (54), page 1, first column, lines 1-3, and in the Specification, column 1, lines 1-3, in the title section, please add the word "Novel" as the first term in the title, before the word "Process." Please delete the term "it's," as it is grammatically incorrect, and insert the term --its-- instead. The title of the patent should read:

--Novel Process for the Preparation of Lapatinib and its Pharmaceutically Acceptable Salts--

IN THE CLAIMS:

In claim 1, column 21, line 5 and column 22, line 5, please bring components of formula (9) into a single compound: --                                                            --

Signed and Sealed this  
Eleventh Day of November, 2014

Michelle K. Lee  
*Deputy Director of the United States Patent and Trademark Office*